US011547168B2

(12) United States Patent
Burry et al.

(10) Patent No.: US 11,547,168 B2
(45) Date of Patent: Jan. 10, 2023

(54) AUTOMATED GOGGLE LENS ROLL-OFF SYSTEM

(71) Applicants: James Michael Burry, Troutman, NC (US); Adrian Richard Tetteh, Huntersville, NC (US)

(72) Inventors: James Michael Burry, Troutman, NC (US); Adrian Richard Tetteh, Huntersville, NC (US)

(73) Assignee: BISS PRODUCT DEVELOPMENT, LLC, Troutman, NC (US)

( * ) Notice: Subject to any disclaimer, the term of this patent is extended or adjusted under 35 U.S.C. 154(b) by 112 days.

(21) Appl. No.: 16/949,293

(22) Filed: Oct. 23, 2020

(65) Prior Publication Data

US 2021/0120905 A1 Apr. 29, 2021

Related U.S. Application Data

(60) Provisional application No. 62/924,937, filed on Oct. 23, 2019.

(51) Int. Cl.
*A42B 3/18* (2006.01)
*A42B 3/26* (2006.01)

(52) U.S. Cl.
CPC .............. *A42B 3/185* (2013.01); *A42B 3/26* (2013.01)

(58) Field of Classification Search
CPC ...................................... A61F 9/025
See application file for complete search history.

(56) References Cited

U.S. PATENT DOCUMENTS

| 3,946,442 | A | 3/1976 | Wallander |
| 4,150,681 | A | 4/1979 | Howarth, Jr. |
| 4,528,701 | A | 7/1985 | Smith |
| 4,633,532 | A | 1/1987 | Yagasaki |
| 5,592,698 | A | 1/1997 | Woods |
| 6,047,412 | A | 4/2000 | Wilson, II et al. |
| 6,370,700 | B1 | 4/2002 | Arion |
| 6,415,452 | B1 * | 7/2002 | Watanabe ............... G02C 7/16 2/438 |
| 6,416,177 | B1 * | 7/2002 | Gibson ................. B08B 17/04 351/158 |
| 6,698,032 | B1 | 3/2004 | Robertson |
| 6,725,467 | B2 | 4/2004 | Harding |
| 8,782,820 | B2 * | 7/2014 | Park ....................... A61F 9/029 351/41 |
| 9,708,154 | B2 * | 7/2017 | Kulik .................... B65H 18/00 |
| 9,839,558 | B2 * | 12/2017 | Blanchard .............. A61F 9/025 |
| 10,123,907 | B2 * | 11/2018 | Sigismondo ........... A61F 9/022 |
| 10,342,704 | B2 | 7/2019 | Blanchard et al. |

(Continued)

*Primary Examiner* — Katherine M Moran

(57) ABSTRACT

An improvement of current lens roll-off systems is provided. The improvement embodies a goggle module operatively associated with a remote module by way of a wireless signal transmitted by a user engaging a remote button of the remote module, wherein the remote module may be removably connected along handlebars of the vehicle. The goggle module has an upper arm and lower arm, wherein the upper arm confirms the presence of the supply canister of the lens roll-off system, and wherein the lower arm engages a pull cord of the lens roll-off systems. The wireless signal urges the pull cord by way of the lower arm, thereby the rider can automatically operate the lens roll-off system hands-free.

7 Claims, 4 Drawing Sheets

(56) References Cited

U.S. PATENT DOCUMENTS

| | | |
|---|---|---|
| 10,426,665 B1 | 10/2019 | Fridie |
| 2008/0276355 A1 | 11/2008 | Lawrence |
| 2009/0229044 A1 | 9/2009 | Gill |
| 2012/0023647 A1 | 2/2012 | Park |
| 2017/0313543 A1 | 11/2017 | Kulik |
| 2017/0354540 A1 | 12/2017 | Yang et al. |

* cited by examiner

AUTOMATED GOGGLE LENS ROLL-OFF SYSTEM

CROSS-REFERENCE TO RELATED APPLICATION

This application claims the benefit of priority of U.S. provisional application No. 62/924,937, filed 23 Oct. 2019, the contents of which are herein incorporated by reference.

BACKGROUND OF THE INVENTION

The present invention relates to riding goggle lens roll off systems and, more particularly, an automated goggle lens roll-off system that will operatively associate with any existing goggle lens roll-off film system, allowing the rider to clear their vision wirelessly, without having to let go of the vehicle.

When riding a motorcycle, mountain bike, off-terrain vehicles, or the like, especially if riding off road, the rider's goggle lens inevitably get covered with mud, dirt, rain, etc., impairing their vision. Riding with impaired vision is a huge safety concern. Luckily there are a lot of goggles on the market that offer roll-off film that covers the goggle lens enabling the rider to roll the film so that the impaired film is removed and replaced with a clean film lens, restoring the rider's vision. However, current roll-off film systems require the rider to let go of at least one of their hands off the handlebars to clear their vision—at the point when the riders' vision is impaired—to pull the cord on the roll-off system, possibly several times, to clear their vision. Riding a motorcycle with one hand can be difficult and dangerous, especially in off-road conditions where these type of goggle systems are often used. But riding with impaired vision is also very dangerous. If the rider is in a situation where he or she cannot let go of the handlebars they are forced to continue riding with impaired vision until they can safely ride with one hand or stop.

As can be seen, there is a need for an automated goggle roll-off system that can attach to any existing goggle lens roll-off system, allowing the rider to clear their vision wirelessly, without having to let go of the handlebars.

The system embodied in the present invention attaches to any goggle lens roll-off system. It has an electrically powered "arm" that grabs or engages the pull cord. When the rider presses the button mounted on their handlebar with their thumb (while also keeping a safe grip of the handlebar grip), a wireless signal is sent to the goggle mounted system. When the system receives the signal, the arm grabbing the roll-off system pull cord makes short, quick pulls of the string which activates the lens clearing mechanism, enabling clear vision at all times.

The present invention enables riders to quickly access the wireless button with their thumb and clear their vision instantly without removing their hands from the handlebars, minimizing the risk of losing control of their motorcycle. Activation of the thumb button is as easy and natural as operating the hand brake or clutch, so a rider will feel comfortable clearing their vision anytime.

The present invention attaches to any goggle with almost any roll-off system since all roll-off systems are currently nearly identical. Therefore users of the present invention can improve their existing goggle roll-off system by attaching the present invention, making their existing system an automated wireless system.

SUMMARY OF THE INVENTION

In one aspect of the present invention, a system for improving a lens roll-off equipment includes the following: a goggle module removably attachable to a goggle utilizing the lens roll-off equipment; an upper arm integrated to the goggle module; a curved interface at a distal end of the upper arm; and a lower arm engaging a pull cord of the lens roll-off equipment in such a way to operatively associate with the pull cord.

In another aspect of the present invention, the system for a lens roll-off equipment includes the following: a remote signal generator removably attachable to a handlebar of a vehicle, a goggle module removably attachable to a goggle utilizing the lens roll-off equipment; a strap mount provided by the goggle module to removably attach to a strap of said goggles; an upper arm integrated to the goggle module; a curved interface at a distal end of the upper arm, the curved interface dimensioned to engage a canister of the lens roll-off equipment; a lower arm engaging a pull cord of the lens roll-off equipment in such a way that activation of the remote signal generator operatively associates the lower arm and the pull cord; a distal end of the lower arm providing a hook to operatively associate with the pull cord; and a proximal end of the lower arm operatively associated with a drive gear having gear teeth extending from less than three-quarters of a circumference of the drive gear, whereby the drive gear acts as a slip clutch.

These and other features, aspects and advantages of the present invention will become better understood with reference to the following drawings, description and claims.

DETAILED DESCRIPTION OF THE INVENTION

Figure 1:
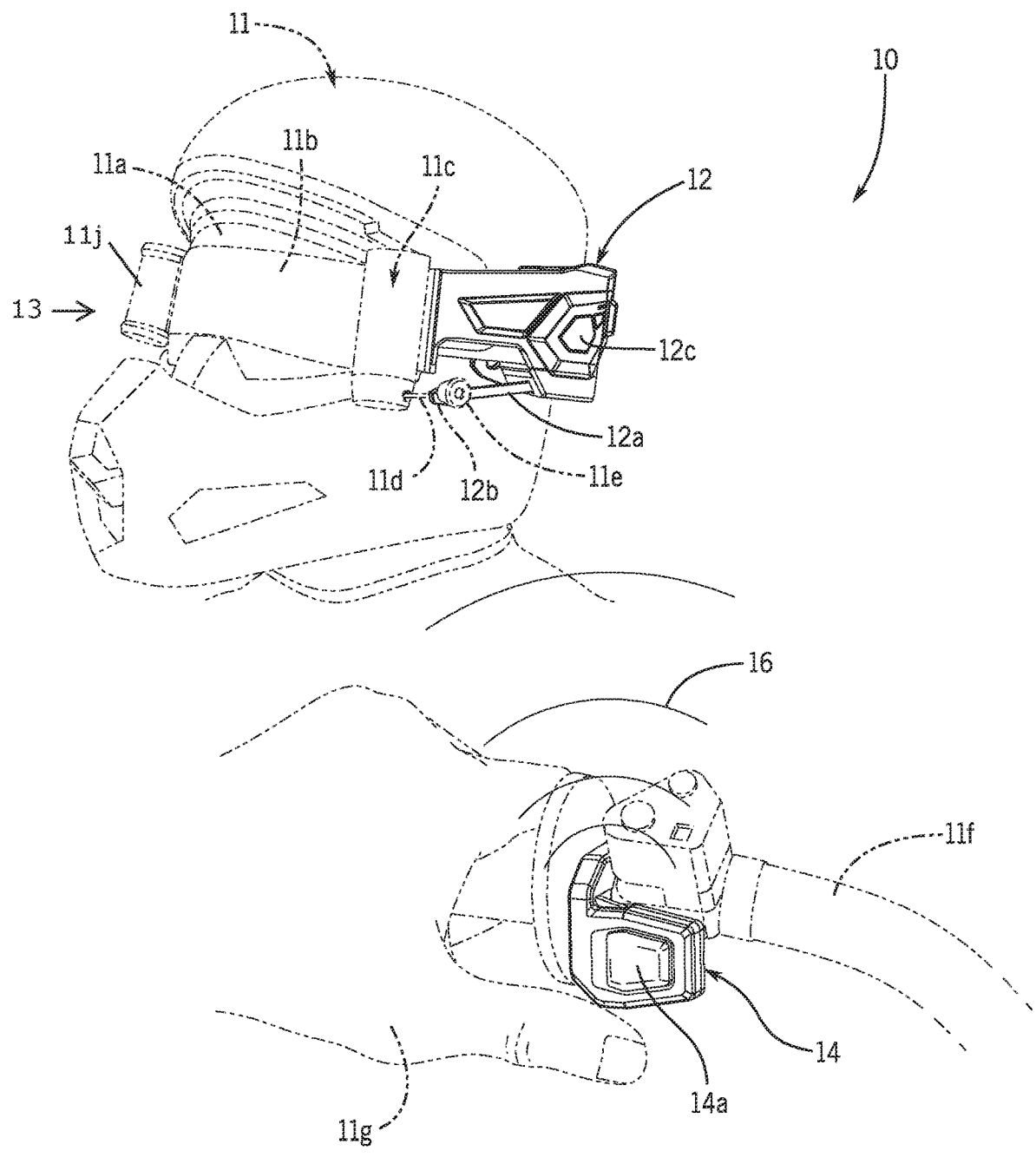
FIG. 1 is a perspective view of an exemplary embodiment of the present invention, shown in use.
Figure 2:
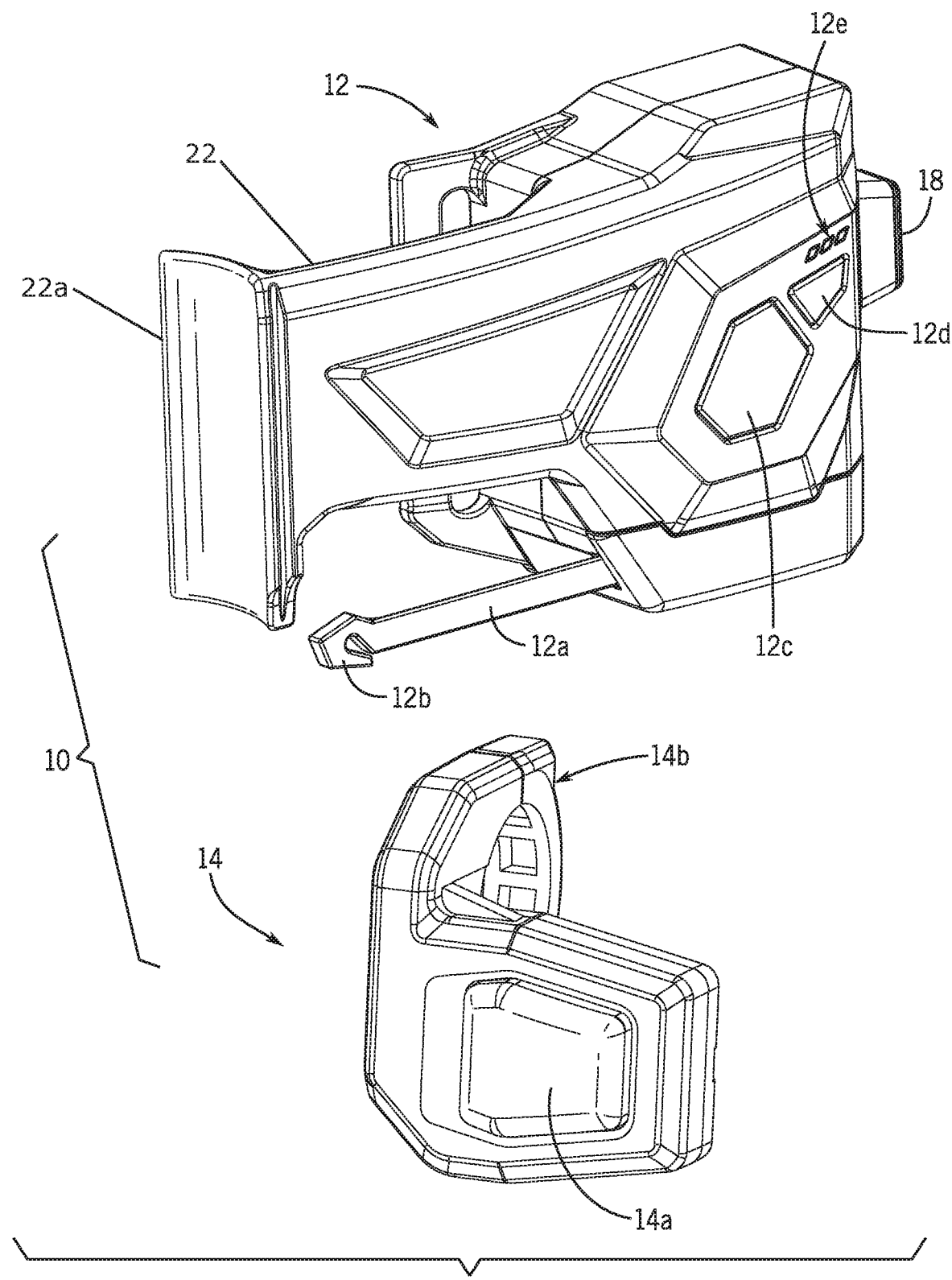
FIG. 2 is a perspective view of an exemplary embodiment of the present invention.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides an improvement of current lens roll-off systems for enthusiasts of off-road motorbiking, bicycling, and all-terrain vehicles. The improvement embodies a goggle module operatively associated with a remote module by way of a wireless signal transmitted by a user engaging a remote button of the remote module, wherein the remote module may be removably connected along handlebars of the vehicle. The goggle module has an upper arm and lower arm, wherein the upper arm confirms the presence of the supply cannister of the lens roll-off system, and wherein the lower arm engages a pull cord of the lens roll-off systems. The wireless signal urges the pull cord by way of the lower arm, thereby the rider can automatically operate the lens roll-off system hands-free.

Referring now to FIGS. 1 through 4, the present invention may include a system 10 for improving a lens roll-off system 13, embodying a method of automating activation of said lens roll-off system 13. A lens roll-off system 13 is typically associated with a goggle 11a and/or helmet 11, wherein a roll-off screen 11b is rollable between a supply roll 11j and an opposing take-up roll 11c, wherein the roll-off screen 11b is (by way of rotation of the take-up roll 11c) is manually activated by a pull cord 11d having a pull cord handle 11e.

The system 10 provides a goggle module 12 operatively associated with a remote module 14 by way of a wireless connection/signal 16 transmitted by a user engaging a remote button 14a of the remote module 14. The remote module 14 may be removably connected along handlebars 11f of a vehicle, wherein the remote module 14 is adjacent to the user's hand 11g when the user is engaging said handlebars 11f. It should be understood that even though the drawings show only handlebars 11f, that some off-road vehicles do not utilize handlebars, and so the remote module 14 can be mounted on a steering wheel and any place on the vehicle that is adjacent to the hands of the driver.

Figure 3:
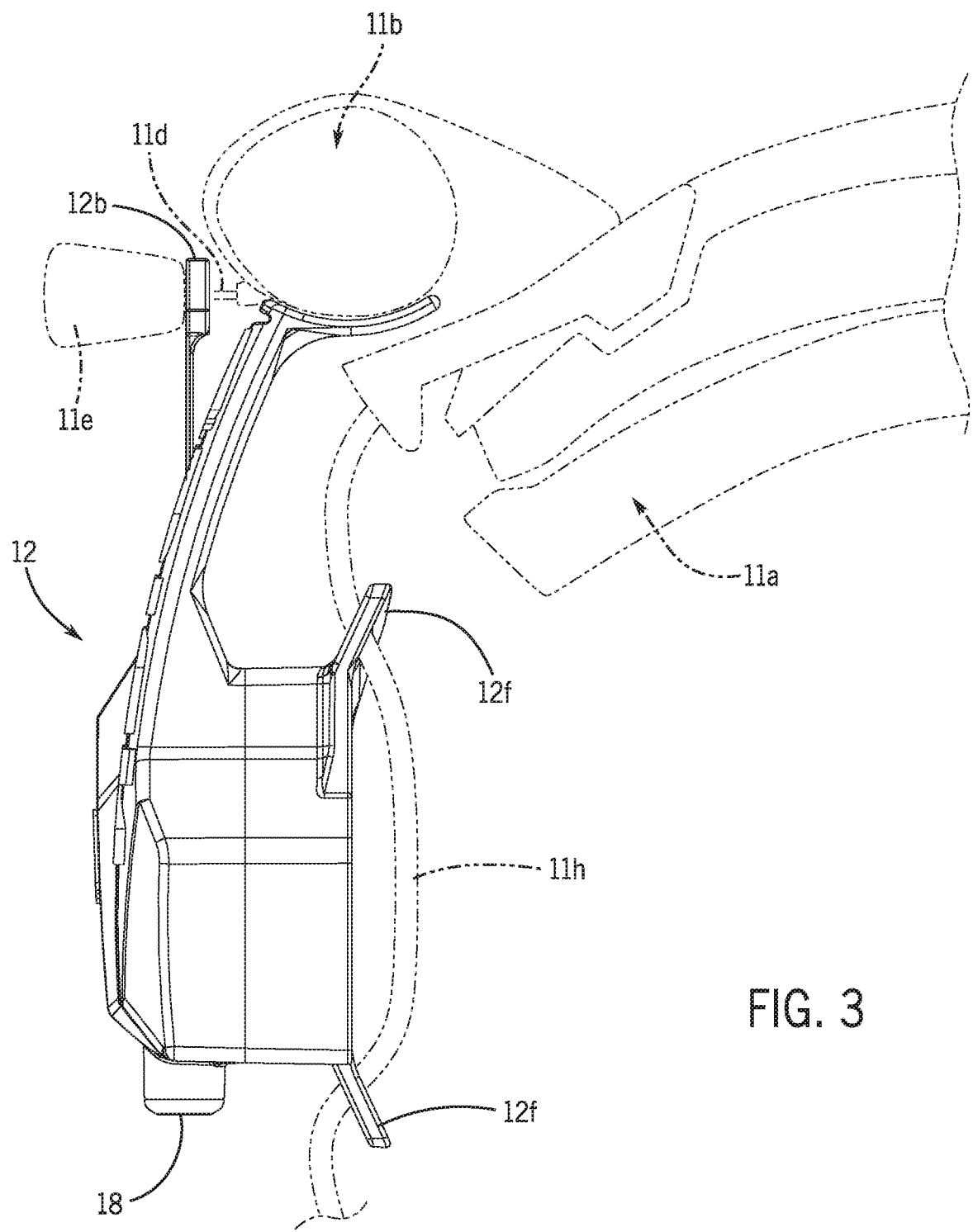
FIG. 3 is a top plan view of an exemplary embodiment of a goggle module of the present invention.
Figure 4:
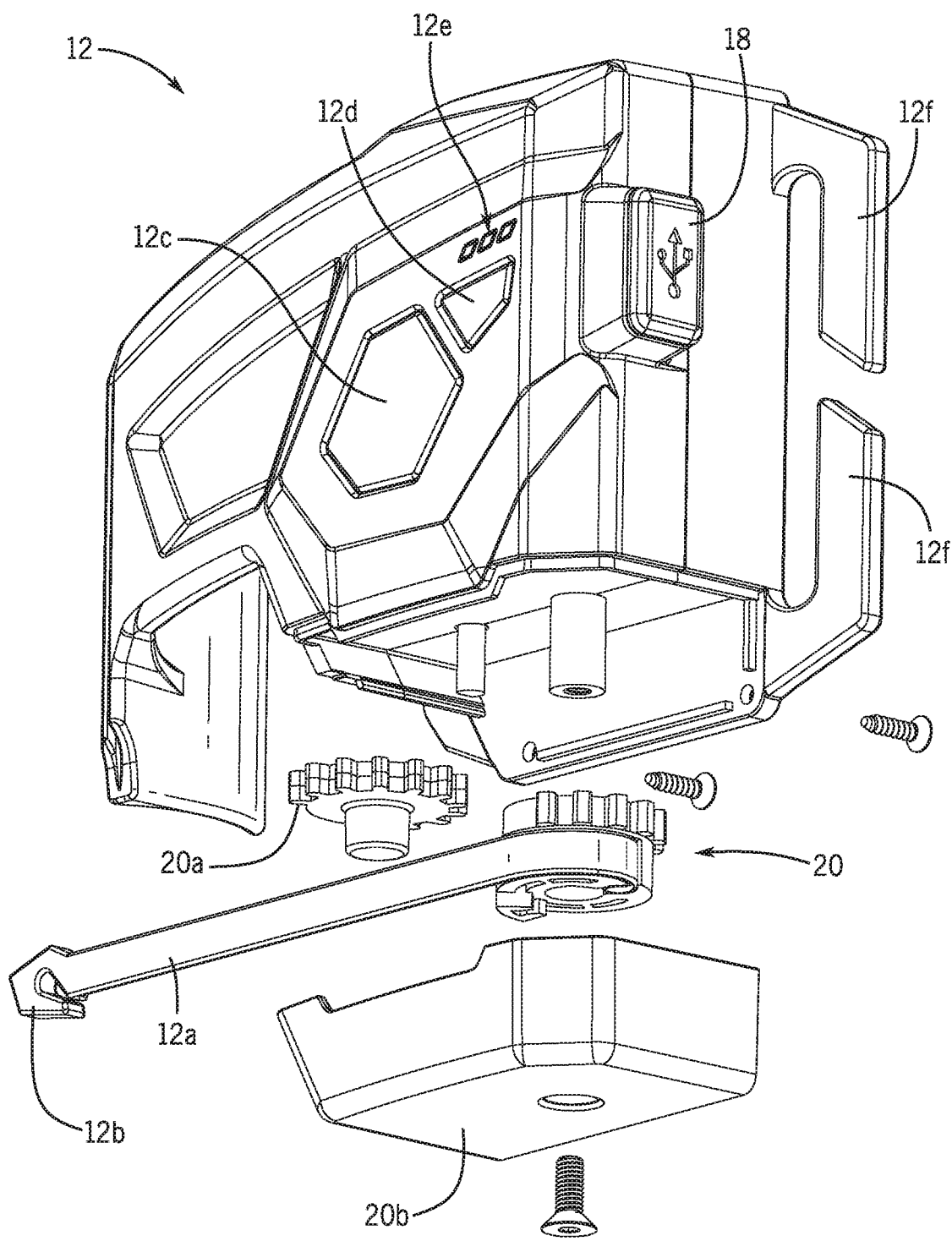
FIG. 4 is a bottom exploded view of an exemplary embodiment of the goggle module of the present invention.

The goggle module 12 may have strap mounts 12f to removably attach to straps 11h of the goggles 11a and/or helmet 11, as illustrated in FIG. 3.

The goggle module 12 may have a body providing the strap mounts 12f. The body may also have an upper arm 22 and a spaced apart lower arm 12a. The upper arm 22 may terminate in a curved interface 22a dimensioned and adapted to about a cylindrical canister of a clean roll 11c. A distal end of the lower arm 12a may include a hook 12b dimensioned and adapted by engaging the pull cord 11d of the lens roll-off system 13.

A proximal end of the lower arm 12a may be housed by a removable cover 20b of the body, wherein the proximal end is operatively associated with a motor-powered (not shown) gear assembly 20 and a drive gear 20a. When the goggle module 12 receives the wireless signal 16, the hook 12b may engage the pull cord 11d by way of the pull cord handle 11e of the roll-off system 13. The drive gear 20a may be mounted directly to the motor/gearbox drive shaft. The drive gear 20a may only have gears on part of its circumference so it also acts as a slip clutch.

The body of the goggle module 12 may also provide a power button 12c, a sync mode button 12d, a power indicator 12e, a USB charging port 18.

A method of using the present invention may include the following. The system 10 may be attached to any goggle/helmet 11h by inserting the goggle/helmet strap 11h through the split hook strap mounts 12f on the back of the outer case/body.

Once mounted on the goggle/helmet strap 11h, the curved interface 22a may be pressed up against the canister 11c of any roll off the system 10, thereby securing and properly locating the system of the present invention viz-a-viz the roll-off system 13. The hook 12b of the lower/pull arm 12a is then engaged to the pull cord 11d from the roll off system 13.

The wireless remote handlebar button 14a is mounted to the handlebars 11f of the motorcycle or other vehicle. It is mounted near the hand grips so the user can operate the button with their thumb without releasing their grip on the handlebars.

When the user presses the remote button 14a it sends a wireless signal 16 to the goggle mounted system 10. When the wireless signal 16 is received by a computer/processor (not shown), the motor (not shown) is powered. When the motor spins, it activates the drive gear 20a, which engages temporarily with the gear assembly 20. This is "temporary" because there are only teeth on part of the circumference of each gear. When the teeth engage, the gear assembly 20 rotates and in turn the hook 12b urges the pull cord 11d. When urged, the roll off system 13 advances clean film 11b in front of the rider's eyes. When the drive gear 20a does not engage, the gear assembly 20 quickly rotates backwards due to the spring tension provided by the goggle roll-off system. This returns the pull arm hook 12b, and roll off system pull cord 11d, back to its original position. This is rapidly repeated several times to fully advance the roll-off screen/film 11b in the roll off system 13 and clear the rider's vision.

In certain embodiments, the time the motor spins with each wireless signal 16, affects the amount of film that is advanced in the roll off system. Additionally, a program could be written to measure the variance of film advanced as the supply roll and the take-up roll diameters change in the roll off system. This would more accurately advance a precise amount of film. This variance is different for every brand roll off and would need to be reset with each use.

It should be understood, of course, that the foregoing relates to exemplary embodiments of the invention and that modifications may be made without departing from the spirit and scope of the invention as set forth in the following claims.

What is claimed is:

1. A system, the system comprising:
    a goggle module removably attachable to a goggle utilizing a lens roll-off equipment;
    an upper arm integrated to the goggle module;
    a curved interface at a distal end of the upper arm; and
    a lower arm engaging a pull cord of the lens roll-off equipment in such a way to operatively associate with the pull cord.

2. The system of claim 1, further comprising:
    a signal generator removably attachable to a vehicle driven by a wearer of the lens roll-off equipment, wherein activation of the signal generator operatively associates the lower arm and the pull cord.

3. The system of claim 1, further comprising:
    a distal end of the lower arm including a hook to operatively associate with the pull cord.

4. The system of claim 1, further comprising:
    a proximal end of the lower arm operatively associated with a drive gear having gear teeth extending from less than three-quarters of a circumference of the drive gear, whereby the drive gear is configured to act as a slip clutch.

5. The system of claim 1, further comprising:
    a strap mount provided by the goggle module to removably attach to a strap of said goggles.

6. The system of claim 1, wherein the curved interface is dimensioned to engage a canister of the lens roll-off equipment.

7. A system, the system comprising:
    a remote signal generator removably attachable to a vehicle,
    a goggle module removably attachable to a goggle utilizing a lens roll-off equipment;
    a strap mount provided by the goggle module to removably attach to a strap of said goggles;
    an upper arm integrated to the goggle module;
    a curved interface at a distal end of the upper arm, the curved interface dimensioned to engage a canister of the lens roll-off equipment;
    a lower arm configured to engage a pull cord of the lens roll-off equipment in such a way that activation of the remote signal generator operatively associates the lower arm and the pull cord;
    a distal end of the lower arm including a hook to operatively associate with the pull cord; and a proximal end of the lower arm operatively associated with a drive gear having gear teeth extending from less than three-quarters of a circumference of the drive gear, whereby the drive gear is configured to act as a slip clutch.

\* \* \* \* \*